United States Patent [19]

Pratt, Jr.

[11] 4,195,643

[45] Apr. 1, 1980

[54] DIAGNOSTIC FORCE ANALYSIS SYSTEM

[75] Inventor: George W. Pratt, Jr., Wayland, Mass.

[73] Assignee: Massachusetts Institute of Technology, Cambridge, Mass.

[21] Appl. No.: 754,370

[22] Filed: Dec. 27, 1976

[51] Int. Cl.$^2$ .............................................. A61B 5/02
[52] U.S. Cl. .................................................... 128/779
[58] Field of Search ............ 128/2 S, 2.05 D, 2.05 E, 128/2.05 P, 2.05 V, 2 P, 2.1 P, 779; 73/719–722, 172, 1 B, 780, 769; 177/210 R, 210 C, 210 EM

[56] References Cited

U.S. PATENT DOCUMENTS

| | | | |
|---|---|---|---|
| 2,800,796 | 7/1957 | Westcott et al. | 73/718 |
| 3,090,226 | 5/1963 | Corti et al. | 73/141 |
| 3,169,022 | 2/1965 | Kretsinger | 177/210 C |
| 3,203,223 | 8/1965 | Petrow | 73/1 B |
| 3,314,493 | 4/1967 | Kennedy | 177/210 C |
| 3,348,568 | 10/1967 | Stork et al. | 361/321 |
| 3,678,378 | 7/1972 | Trott et al. | 177/210 C X |
| 3,712,294 | 1/1973 | Muller | 128/25 |
| 3,782,486 | 1/1974 | Kuhn et al. | 177/210 C |
| 3,894,437 | 7/1975 | Hagg et al. | 128/25 |
| 3,906,931 | 9/1975 | Terekhov | 128/25 |
| 3,912,029 | 10/1975 | Gorman et al. | 177/210 R |
| 4,102,422 | 7/1978 | Christiansson | 177/210 C |

OTHER PUBLICATIONS

"An Outstanding Tool in Biomechanics: Quartz Multi--Component Measuring Platform"–Kistler Instruments, Winterthur, Switzerland 1974.

Pratt, G. W. "Lameness & Condition Determined by Force Plate Measurements," Hoofbeats 1974 v. 42 #10 p. 106.

Stokes, I. A. F. et al. "Force Distributions Under the Foot-A Dynamic Measuring System," Biomed. Engr., V. 9 #4 1974 pp. 140-143.

Cappozzo, A. et al. "A General Computing Method for the Analysis of Human Locomotion, " J. Biomechanics V. 8 pp. 307-320 Sep. 1975.

Ray, C. D., *Biomedical Measurement Systems* (Ch. 15), in Medical Engineering, Yrbk Publ., Chic. 1974, pp. 149-152.

Pedotti, A. "Simple Equipment Used in Clinical Practice for Evaluation of Locomotion," IEEE Trans. on Biomed. Engr., vol. BME-24, No. 5, Sep. 1977 pp. 456-461.

Pratt, G. W. et al., "Force Plate Studies of Equine Biomechanics," Amer. Jnl. Vet. Research, v. 37 #11, Nov. 1976 pp. 1251-1255.

Weitzman, D. O. et al., "Quantification of Chorea in Huntington's Disease By Power Spectral Analysis," Diseases of the Nervous System, vol. 37, pp. 264-268 May, 1976.

*Primary Examiner*—Robert W. Michell
*Assistant Examiner*—Francis J. Jaworski
*Attorney, Agent, or Firm*—Arthur A. Smith, Jr.; Robert Shaw

[57] ABSTRACT

A system operable to measure the time varying forces transmitted by a body and to combine the forces transmitted by different parts of the body. The system can be employed to measure physiological forces associated with motion of the body such as the gait of humans or animals. It can also be employed to measure forces internally generated by the body at rest such as ballistocardiographic and posture control forces. The posture control forces can be used as a measure of lameness. The Fourier transform of the force ballistocardiogram and posture control forces are found to contain information related to physiological condition. In some configurations the system employs ceramic capacitors as piezoelectric force transducers in a special circuit. The use of ceramic capacitors as pyroelectric bolometers is also discussed.

4 Claims, 27 Drawing Figures

HEEL STRIKE (YOUNG MAN)

FIG. 11

HEEL STRIKE (MIDDLE AGED MAN)

DIAGNOSTIC FORCE ANALYSIS SYSTEM

The present invention relates to systems operable to measure physical inputs such as force, pressure and/or temperature, to measure, with great accuracy and consistency, changes therein of the order of one part in 4000 and less, and when required, to analyze the input signals on the basis of some established standard.

The present invention relates to a system operable to measure forces transmitted by the human or animal body both static or dc and dynamic or ac. These forces may be due to the motion of the body as in the gaits of humans; they may arise as the result of an external excitation of the body such as the force transmitted from a first part of the body to a second part as the result of a mechanical excitation at the first part and its detection by a force transducer—which includes the use of a microphone— at the second part. The forces measured by the system further include forces internally generated by the body such as, for example, those arising from the action of the heart, the forces created by a fetus, forces associated with posture control, tremors, and involuntary muscular action.

In carrying out these measurements it is highly desirable to have a force transducer system capable of wide dynamic range. Forces in the 1000 Kg range are encountered with the galloping horse and decreasing to perhaps 20 grams for the fetal heart beat. It has been found that commercial ceramic capacitors, e.g., Erie #1831-050-651-105 M, 1 #f can act as an inexpensive wide range, and extremely low noise dynamic force transducer when combined with low noise filters. It has been found that frequencies in the ranges ~ 0–1 Hz, 1–10 Hz, and 10–50 Hz and 0–2 kHz are particularly useful to examine.

The invention herein has broad implications in that the inventor has found a very sensitive, but stable, sensor which he has combined with diagnostic circuitry to permit fabrication of, for example, portable, relatively inexpensive apparatus to perform diagnostic analysis with regard to force-related, body functions and the like of humans and animals; but the apparatus can be used to diagnose force-related functions in mechanical equipment, as well. Hereinafter, a few aspects of the invention are gone into in detail, whereas others are just touched upon. A great deal of work in connection with the system herein described was done with humans and horses as the test species and most of the testing related to "forcefootprints" (i.e., force vs. time traces of the steps of the species tested), ballistocardiograms, and measurements of the internal forces generated by the body at rest (i.e., force vs. time traces of forces associated with the posture control system of the body).

For over 100 years studies have been made of the forces associated with locomotion of the body of man or of animals. M. Marey published "De La Locomotion Terrestre Chez Les Bipedes et Les Quadrupedes", in Annales des Sciencies Naturelles—Zoologie Vol. 16, page 1 (1872). Records of the force associated with a step throughout the time duration of the step were made. They led to a basic understanding of the mechanics associated with the various gaits in two-and four-footed creatures. Since that time many studies have been made for the purpose of designing artificial limbs; see a journal article by D. Cunningham and G. Brown, "Two Devices for Measuring the Forces Acting on the Human Body During Walking" which appeared in and the work of C. Hirsch and I Goldie, "Walway Studies after Intertrochanteric Osteotomy for Osteoarthritis of the Hip", Acta orthop. Scandinav. 40, 334 (1969). In all of these works the forces were measured using equipment that required a laboratory environment with the force sensitive plates either set into the floor or built into a special platform. These plates were not easily portable, inexpensive devices that could be made widely available. An excellent example of the complexity of current force plates for gait analysis is given by J. Skorecki, J. Strain Analysis, 1, 429 (1966).

Accordingly, it is an object of the present invention to provide a force-plate system which is rugged, simple, relatively inexpensive, portable and one which has a low profile so as not to require special installation so as not to disturb the steps of a species being examined.

Another object is to provide a force-plate system which can be used in a doctor's office or in a stable or in some other location in which special preparation of the surface upon which the plate rests is minimized.

Still another object is to provide a force-plate system that is useful for measuring the "force foot-print" of a species, be that species human or animal.

When the heart beats, small forces and consequently a very slight motion is imparted to the body and the record of the corresponding force or displacement is known as force ballistocardiogram or displacement ballistocardiogram. Ballistocardiography is a well established field of heart research in humans, see C. K. Friedbert, "Diseases of the Heart," Saunders Co. (1966). A study of a ballistocardiogram can reveal information relevant to cardiovascular disease but also can be directly correlated with the physical condition of athletes, in particular with their staying power (E. Jokl, Am. J. Cardiology 19, 105 (1959)). These measurements have traditionally been made by strapping the patient in a specially suspended bed and watching the minute motion of the apparatus. This is an extremely inconvenient and expensive method for the study of humans and hardly an acceptable method for the study of horses. The system disclosed herein is capable of measuring the force ballistocardiogram taken by simply having the subject stand or sit on the force plate. Because of the great sensitivity of the piezoelectric transducers (in the form of ceramic capacitors), the measurements can be taken with relatively simple equipment. Further processing of the force ballistocardiogram by filtering the frequency content of the output of the force transducer and further processing by taking the Fourier transform of said output provides new information concerning the cardiovascular system. This information includes the natural resonant frequency of the lumped circuit representation of the cardiovascular system and the damping of said system. Interestingly, the present inventor has found that a horse will in many instances stand quietly on the plate and reproducible measurements of the animal's heart forces can be easily made. It is believed that the ballistocardiogram of a horse hereinafter discussed is the first force ballistocardiogram recorded for a horse. This was first published in "Lameness and Condition Determined by Force Plate Measurements" G. W. Pratt, Jr., Hoofbeats Vol 42, No. 10, p. 106 (1974). Force plates have been used for early diagnosis of psychomotor deficiencies in children. The plate described here should have similar diagnostic capabilities in horses e.g., locating locomotoraxtia ("wobbles") and have been used as described herein to analyze lameness.

As will be evident later in the specification, the forces applied by a live being upon a force plate are many; some are quite large, whereas others are small; and the forces are ac and dc in nature. In an electromechanical system of the type herein disclosed, it has been found that some of the forces can be filtered best by mechanical type filtering while others can be removed best by electrical filtering of the signals representing the forces.

A still further object, therefore, is to provide a force-plate system which is adapted to filter predetermined force signals to emphasize others.

Another important medical area is that of noting the condition of a metallic implant or the like within a body, when the implant is first introduced and after it has been in place for some time, to determine, say, the mechanical properties of the implant. For example, the metallic implant or pin used in the replacement of the human hip joint often becomes loose. The force sensing system disclosed can be used to give a non-invasive indication of the state of the pin. Still another object, then, is to provide a force sensing system that can be employed in connection with the testing of the mechanical state of such implants.

In any of the foregoing systems, it is important to sense the various forces present, but it is also important to sense how such forces differ from some pre-established norm. Hence, a still further object is to provide analyzing circuitry that reduces measurable human subject analysis of the data derived from a sensor.

These and still further objects are addressed hereinafter.

The foregoing objects are achieved in a system for measuring a physical input such as a mechanical force or pressure, for example, and to note very small changes therein. The system includes transducer means that receives said physical input and produces an output voltage that is proportional to the physical input, the output voltage having the relationship ratio to the physical input in at least about $1/10^6$. Impedance means having a very low noise level is connected to the transducer means, and analyzer means is connected to sense said input voltage and to relate the same to said physical input and changes therein.

The invention is hereinafter described with reference to the accompanying drawing in which.

In the explanation that follows, the invention is described mostly with respect to forces that emanate from a live being, here humans and horses. Such forces arise from different physiological sources with the particular species, some are large, some are quite small, some are ac in nature, others dc, and the ac force signals from one source usually differ significantly in frequency from those that originate with another source. Any sensing mechanism and/or analyzing circuitry must measure dynamically, must have a wide dynamic range, frequency selectivity and high signal-to-noise ratio, among other things.

To sense a particular force signal, it usually is necessary to remove by filtration the unwanted signals. This can be done mechanically, or electrically or by a combination. For example the system labeled 101A in FIG. 1 includes a transducer 1A and analyzer or analyzer means 2A; either or both can provide filtration. The transducer can be a single force sensitive element such as 1M in FIG. 9, or an array of interconnected elements such as in FIG. 4. Thus, the transducer can consist of the force plates labeled $1C_1$ and $1C_2$ in FIG. 3 which receive forces $F_1$ and $F_2$ which may emanate from a human or other living body 20. As later explained herein, the forces $F_1$ and $F_2$ are converted to voltage signals, often by piezoelectric devices, and the voltage signals are connected to an analyzer for analysis. The following terms will be used throughout: F is the total force, i.e., here $F = F_1 + F_2 + \ldots F_n$; V is the total voltage and $V = V_1 + V_2 + \ldots V_n$, wherein $V_1, V_2 \ldots V_n$ are composite voltage signals representing $F_1, F_2 \ldots F_n$, respectively. The discussion herein relates in particular to the case where n=2. It will then be seen that the outputs can be analyzed in terms of $F_+ = F_1 + F_2$ and $F_- = F_1 - F_2$, i.e., $V_\pm = V_1 \pm V_2$.

Figure 1:
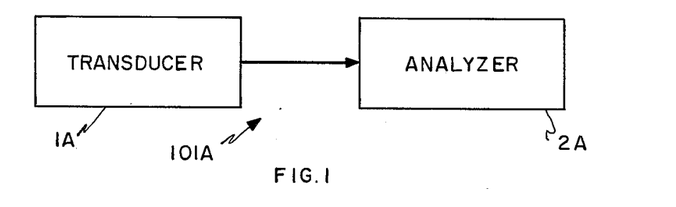
FIG. 1 is a block diagram representation of a system in accordance with the present invention for measuring input force signals and including a transducer and an analyzer.
Figure 5:
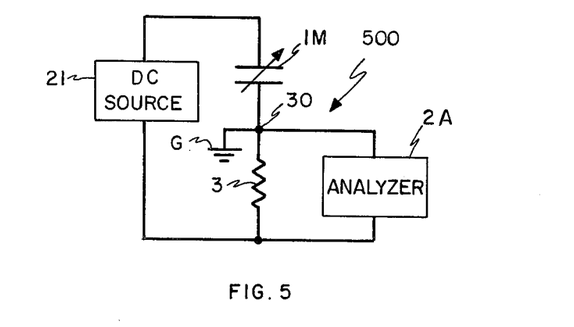
FIG. 5 is a schematic circuit diagram, partly block diagram in form, that includes a capacitor used as a variable transducer.
Figure 6:
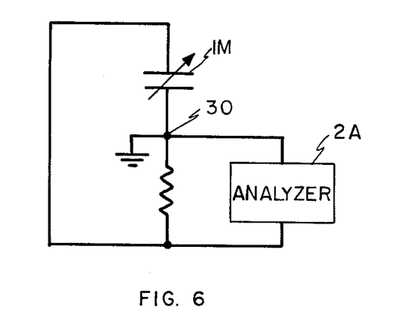
FIG. 6 is a diagrammatic representation of a modification of the circuit of FIG. 5, wherein the transducer is self-powered.

The system 101A in FIG. 1 can be employed as indicated, to measure forces and changes therein. The transducer, in the preferred embodiment, is a ceramic capacitor (model no. 8131-050-651-105 M, manufactured by Erie Technological Products), that exhibits piezoelectric behavior and is adapted to receive a force (i.e., pressure). Appropriate circuitry is shown in FIGS. 5 and 6 wherein the transducer is marked 1M and is indicated to be variable. In fact, the transducer 1M is a capacitor which exhibits piezoelectric behavior, that is, if the device 1M is squeezed its capacitance changes and, importantly, it also generates a voltage that is proportional to the pressure and that voltage appears at its terminals. Thus, with reference to FIG. 9 wherein the transducer shown is again designated 1M and is embedded in a RTV rubber casing or pad 23, vertical forces exerted on the pad 23 will result in a voltage between leads 22A and 22B. Therefore, the transducer 1M can be used in a circuit like that of FIG. 5 which includes a dc source 21 or the transducer 1M can be used in a circuit like that of FIG. 6 wherein the only signal voltage applied to the analyzer 2A is that emanating from the transducer 1M and generated as piezoelectric outputs when mechanical forces are applied to the transducer 1M. In either case the transducer 1M acts as a voltage source whose outputs voltage V changes substantially in response to an applied mechanical force F exerted thereupon, the ratio ($\Delta V/\Delta F$) being at least the order of $10^{-6}$ volts per gram of said force. A resistor 3 is connected in series with the capacitor, the common point (i.e., the point labeled 30) between the resistor and the capacitor being connected to ground G. The resistor-capacitor combination has a time constant that is large compared to the time rate of change of the force F and the combination, as well as the other mechanism and electrical elements in the system 101A, have very low noise levels (i.e., 0.2 $\mu V$). The dc source 21 is a floating source and the analyzer 2A measures the voltage across the resistor or impedance 3. The resilient pad 23 serves to couple mechanical forces to the device 1M and it serves, as well, as a mechanical filter as to spurious ac signals.

Figure 3:
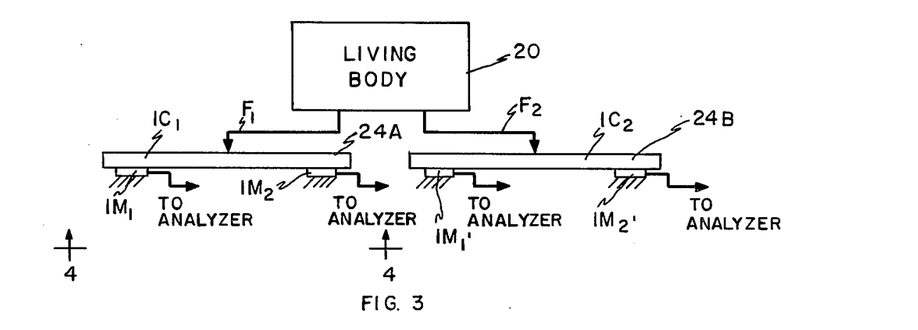
FIG. 3 shows diagrammatically a dual force plate system receiving multiple forces.
Figure 4:
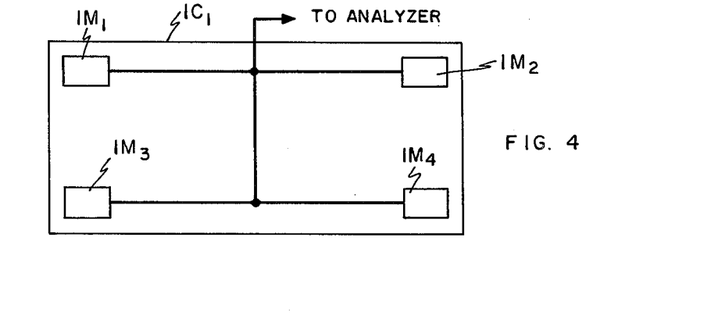
FIG. 4 is a view taken upon the lines 4—4 in FIG. 3, looking in the direction of the arrows, and shows the underside of one of the force plates of FIG. 3 with a particular array of force sensors, one at each corner of the plate.
Figure 9:
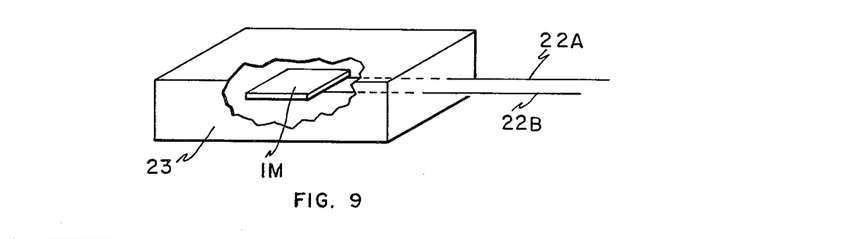
FIG. 9 is an isometric view, partly cutaway, and showing a sensor, like the four sensors mentioned with respect to FIG. 4 above, embedded in a rubber housing.

Most of the work leading to the present invention was done (and continues) using systems that include force plates singly as in FIG. 4 or dual-forceplate systems as shown in FIG. 3. The force plates $1C_1$ and $1C_2$ can be identical; each consists, in systems tested, of a rigid aluminum plate, i.e., 24A and 24B, respectively, about two feet wide by two feet long and one-half to three-fourth inches thick and having force transducers $1M_1, 1M_2 \ldots$ and $1M_1, 1M_2 \ldots$, respectively, each such force transducer being a device, like the device 1M, embedded in a resilient pad as shown in FIG. 9. For present purposes, let it be assumed that the numeral 20 in FIG. 3 represents a human standing on the plates $1C_1$ and $1C_2$ and that the forces $F_1$ and $F_2$ represented respectively the force exerted by the right foot and the left foot of the human. In this circumstance, the dc force $F = F_1 + F_2$ represents the total weight of the human and there are in the force F ac forces that represent, mostly, ballistocardiac forces. The force $F = F_1 - F_2$ can represent a dc force indicating a difference in the forces exerted by the right and left feet of the human and ac forces indicating balance forces, breathing forces, tremors and so forth. In general, breathing forces are in the range 0–1 Hz, the heart forces 1–10 Hz and tremors in the range 10–100 Hz. Careful electrical and mechanical filtration can isolate a particular force.

Figure 2:
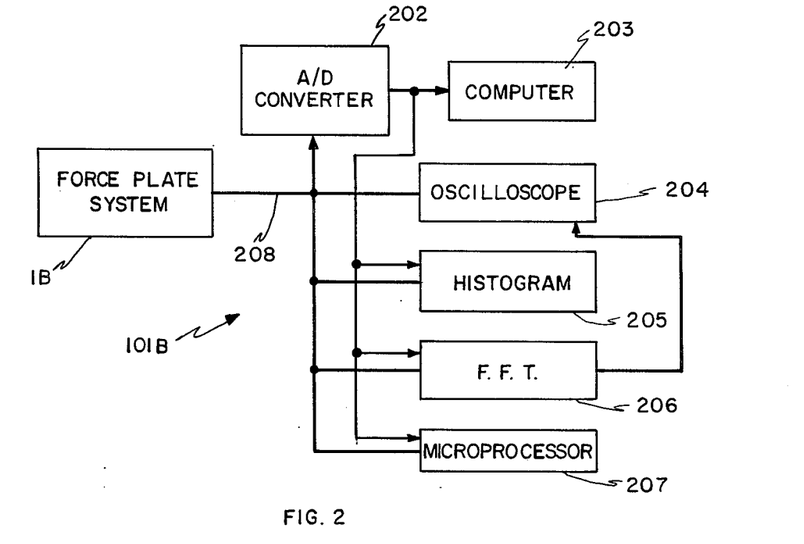
FIG. 2 shows in block diagram form a system wherein the transducer of FIG. 1 is a force plate system and the analyzer takes a number of alternate or complementary forms.
Figure 10:
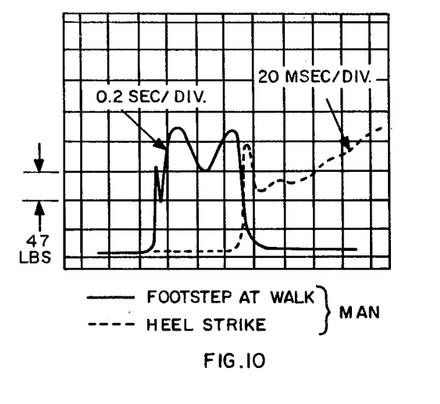
FIG. 10 is a force vs. time trace showing the footstep trace of a man.
Figure 11:
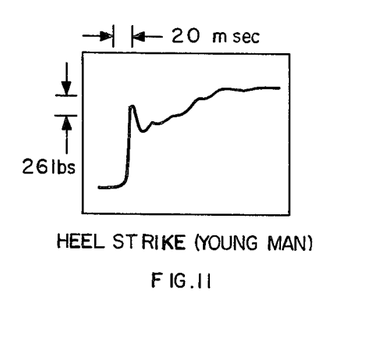
FIG. 11 is a force vs. time trace showing the heel strike of a young man, that is, the initial portion of the step forces is greatly expanded.
Figure 12:
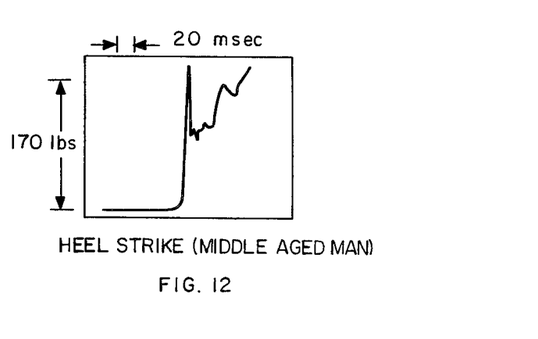
FIG. 12 is a trace, like that of FIG. 11, except for a middle-aged man.
Figure 15:
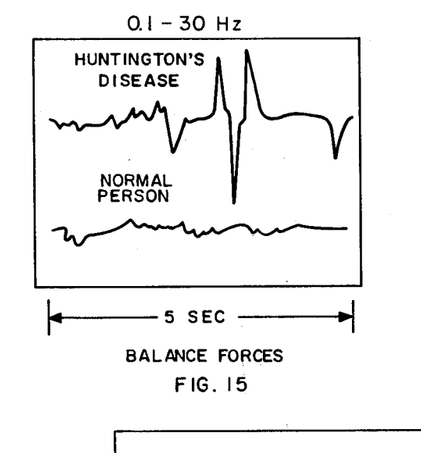
FIG. 15 shows the force vs. time trace representing balance forces taken from a person with Huntington's disease and a person without such disease.
Figure 16:
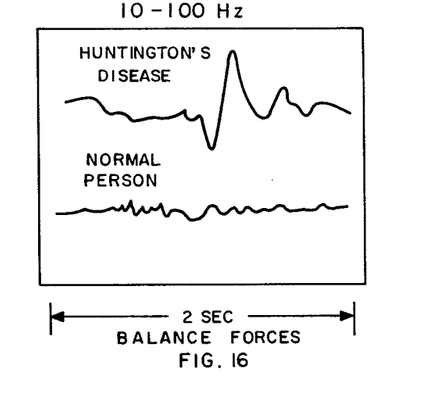
FIG. 16 is a force vs. time trace similar to the trace of FIG. 15 but in a different time scale.

The system shown at 101B in FIG. 2 includes a force plate system 1B which may consist of one or more force plates or combinations of force transcducers disposed to measure a force generated by motion of a body (human or animal) by the response of that body to external forces, or by forces generated internally by the body. The output labeled 208 of the force plate system may be a single signal or a plurality of signals. These signals may in some instances be processed and recorded or displayed in analog form such as shown in FIGS. 10–16. By passing these signals through filters, particular frequency ranges can be selected as shown in FIG. 15 and FIG. 16 and by employing differing time bases, the signals can be displayed as shown in FIG. 10, FIG. 11, and FIG. 12. The use of a storage oscilloscope 204 or transient capture device is of particular value in displaying the measured signals. Digital processing of the signals 208 from the force plate system 1B is, of course, of great value. An A/D converter 202 with appropriate interface components can supply digitized signals to a computer 203, fast Fourier transform (FFT) device 206, microprocessor or microcomputer 207, or other data processing equipment. The data from the force plate system 1B is generally in the form of one or more stationary time series. Consequently, the analysis of such data including statistical, correlation, and forecasting theory is of considerable value in interpreting the experimental results. An example is the histogram 205 discussed later in detail.

FIG. 3, as above indicated, shows a multiple force plate system. Valuable information has been obtained using two force plates such as $1C_1$ and $1C_2$, each having an array of force transducers such as $1M_1 \ldots$ A human standing on the on the plates $1C_1$ and $1C_2$ transmits forces to the plates through his legs. If, as above indicated, these forces $F_1$ and $F_2$ in FIG. 3 are summed, one obtains as a dc signal the body weight and as an ac signal certain forces that are internally generated such as the force ballistocardiogram, respiration, related forces and fetal movements, fetal heartbeat, and the like. If the forces $F_1$ and $F_2$ are subtracted from one another, the principle signals observed are the posture control forces, respiratory forces, tremors, and involuntary muscular movements.

The signal outputs of the four force transducers $1M_1 \ldots 1M_3$ in FIG. 4 are combined. Various such arrays are possible. An array is represented as a lumped or combined capacitance as the capacitance 1M in the circuit marked 500 in FIG. 5. The common ground G in the circuit 500 is of particular importance in achieving a low noise input to the analyzer 2A. A low noise level of 0.2 μm has been readily obtained in practice. Since the ceramic capacitors generally used as transducers in preferred systems are piezoelectric, they generate a voltage as the result of an applied force, and, as above stated, the dc source 21 can be omitted, as shown in FIG. 6. It is good practice to apply a voltage to the capacitors for a time prior to their use in a circuit as in FIG. 6. After discharging the capacitors, they may then be used without the dc supply 21, but with a decreased sensitivity.

Figure 7:
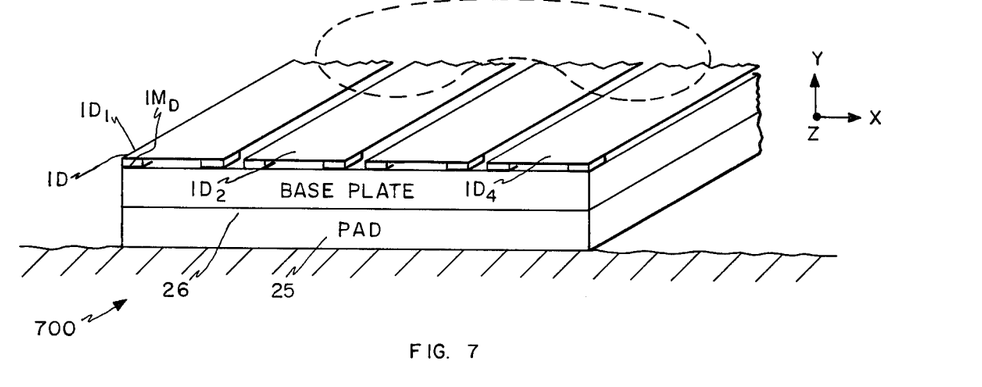
FIG. 7 is an isometric view of a force plate that consists of a plurality of longitudinal sub-plates, laterally separated from one another and resting in a base plate and resilient pad.

FIG. 7 shows a segmented force plate system 700, wherein a series of separate uncoupled force plates or segments $1D_1$, $1D_2$, etc. are combined into a single instrument. Each separate plate provides its own output signal. It is good practice to provide the base plate 26 for the force plate or plates to rest upon. This may be an aluminum plate say ¼ inches thick. The separate force transducers $1M_D$ etc., in FIG. 7 (which may be like the particular embodiment 1M in FIG. 9) can be cemented to both the bottom surface of the force plates or segments $1D_1$, etc. and to the base plate 26. Aluminum plates generally ½ thick have been successfully used as force plate material. One desires a light plate with enough stiffness so that its mechanical resonances lie above the physiological frequencies of interest.

Figure 8:
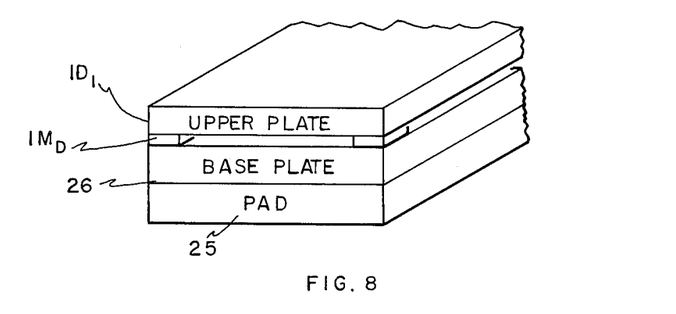
FIG. 8 is an isometric view of one of the sub-plates of FIG. 7.

A detail of a single segment is shown in FIG. 8. The upper plate $1D_1$ in FIG. 8 has an array of force transducers affixed to it in the manner previously discussed. This array rests on and may be affixed to the base plate 26 which in turn rests on the pad 25 which can adapt the system to uneven surfaces. Ensolite pads have shown very effective for this purpose and also serve to isolate the force plate from ground vibrations.

A force transducer 1M as shown in FIG. 9 which has been used with great success has been a ceramic capacitor such as an Erie 1 μf Red Cap capacitor encapsulated in a resilient mount 23. A synthetic mount having a 60 or 80 durometer has been used successfully and operation has been improved by laying a stiff material above and below the capacitor in FIG. 9 before encapsulation. RTV rubber has been employed as encapsulation material. The capacitor leads 22A and 22B bring the signal out of the force sensitive pad 23.

Figure 22:
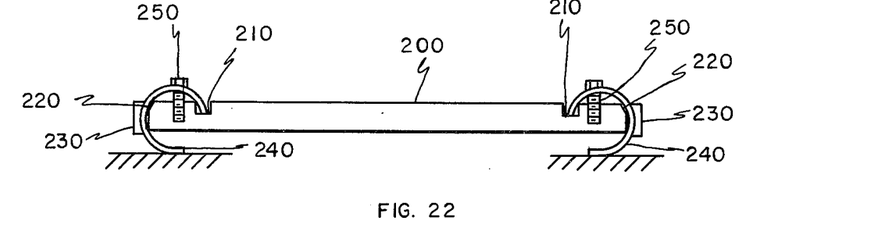
FIG. 22 shows a particular force plate design using strain gauges as the force transducer.

A force plate system has been made using wire wound and semiconductor strain gages. These systems, although not as sensitive as those using ceramic capacitors do allow easy measurement of true dc signals. One such configuration using strain gages is shown in FIG. 22 wherein a plate 200 is shown with grooves 210 cut in it and beveled edge 220 at the upper corner. A pipe or tube at 240 is slotted so that one edge rests in a groove 210, part bears on the edge 220 and it is fixed to the plate 200 by bolts 250. Strain gages 230 are placed on the outside surface, the inside surface, or on both surfaces of the tubes 240. These gages form part of the usual bridge circuitry.

There now follows a discussion of some of the data obtained with the force plate systems. FIG. 10 shows the foot step force vs. time trace for a man walking. The dotted curve is an expansion of the heel strike spike shown at the left of the full curve. It has been observed that the nature of the impact of the limb upon the ground is closely related to lameness and the pre-lame conditions wherein a loss of control of said impact commences with consequent damage to various components associated with locomotion such as the joints, tendons, muscles, and the like. In order to fully reproduce the impact forces as shown in more detail in FIGS. 11 and FIG. 12, the force plate system must not have a natural mechanical or electrical resonance in the range of frequencies of physiological interest. Toward this end the present inventor teaches the use of plates 24A, 24B . . . of sufficient stiffness so that the fundamental mechanical frequency is at least 500 Hz. FIG. 11 shows the heel strike forces of a young man during which considerable energy absorption takes place in the body. FIG. 12 shows the heel strike of a middle aged man of approximately the same body weight as in FIG. 11. Higher forces and less energy absorption is apparant. Presumably the aging process decreases the ability to absorb impact energy. Very similar results have been obtained with horses showing marked increase in impact forces when the animal is lame or is fatigued. Consequently an application of the present force plate system is to evaluate the soundness of the gait, particularly in athletes and race horses.

In order to take traces such as shown in FIG. 10 using the ceramic capacitor transducer as shown in FIG. 5, FIG. 6, and FIG. 9, the circuit impedance is adjusted to provide an RC time constant longer than the event to be measured. A particular embodiment is shown in FIG. 5 and FIG. 6 wherein the impedance is the resistor 3.

Attention is now directed to the measurement of forces internally generated by the body at rest. First, in FIG. 13, there is shown the force ballistocardiogram of a horse standing with both front feet on one plate. The forces associated with a single heart beat are shown. This is an ac force that consists of $F_1+F_2$, where $F_1$ and $F_2$ are the forces transmitted to the plate by the right front and left front legs, respectively. This heart beat force looks very much like that due to the human heart and resembles the response of a damped oscillator to an impulse excitation. Accordingly, a lumped circuit model of the cardiovascular system can be formulated as shown in FIG. 23.

Figure 23:
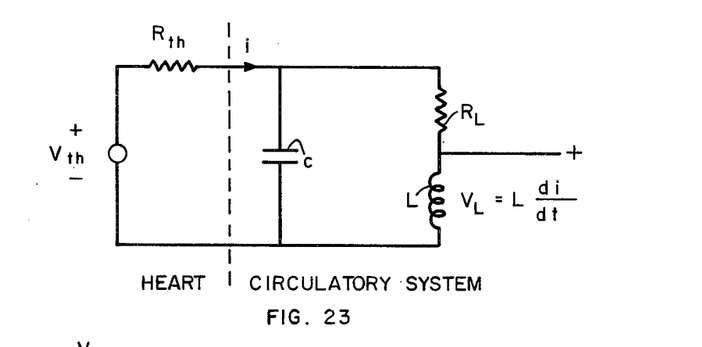
FIG. 23 shows an equivalent circuit representation of a simple model of the cardiovascular system.
Figure 24:
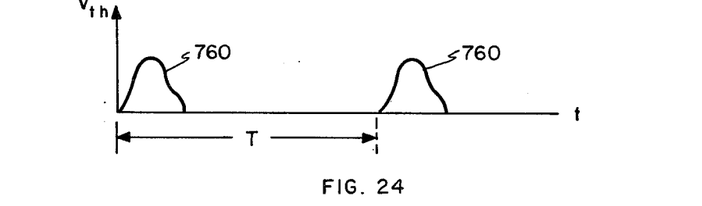
FIG. 24 represents the equivalent Thevenin voltage output of a heart.

The heart, in the lumped circuit model of FIG. 23 wherein the labels represent the lump circuit elements as well as electrical values thereof, is regarded as a Thevenin voltage source $V_{th}(t)$ representing the pressure P(t) at the aorta. The capacitor found at C in FIG. 23 models the compliance of the circulatory system, the resistance labeled $R_L$ is related to losses or energy dissipation in the circulatory system and the inductor shown as L models the inertial effects of the circulating blood. The force plate measures momentum changes which are modeled as the voltage L(di/dt) across the inductor L. L models the blood mass and the current i the blood velocity. The data shown in FIG. 13 can be related to the specific values of the circuit elements shown in FIG. 23, and the Thevenin model of the heart is shown in FIG. 24, where T is the time between pulses. The pulse shape, i.e., P(t), is shown as 760 in FIG. 24. The Thevenin resistance is shown as $R_{th}$.

Figure 13:
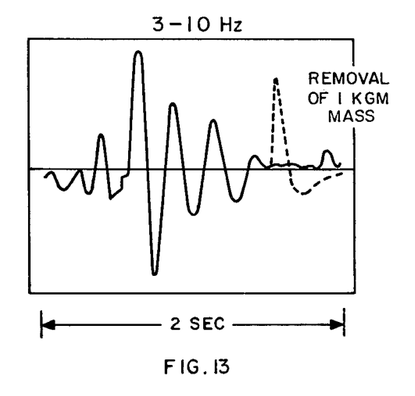
FIG. 13 is a force ballistocardiogram of a horse.
Figure 17:
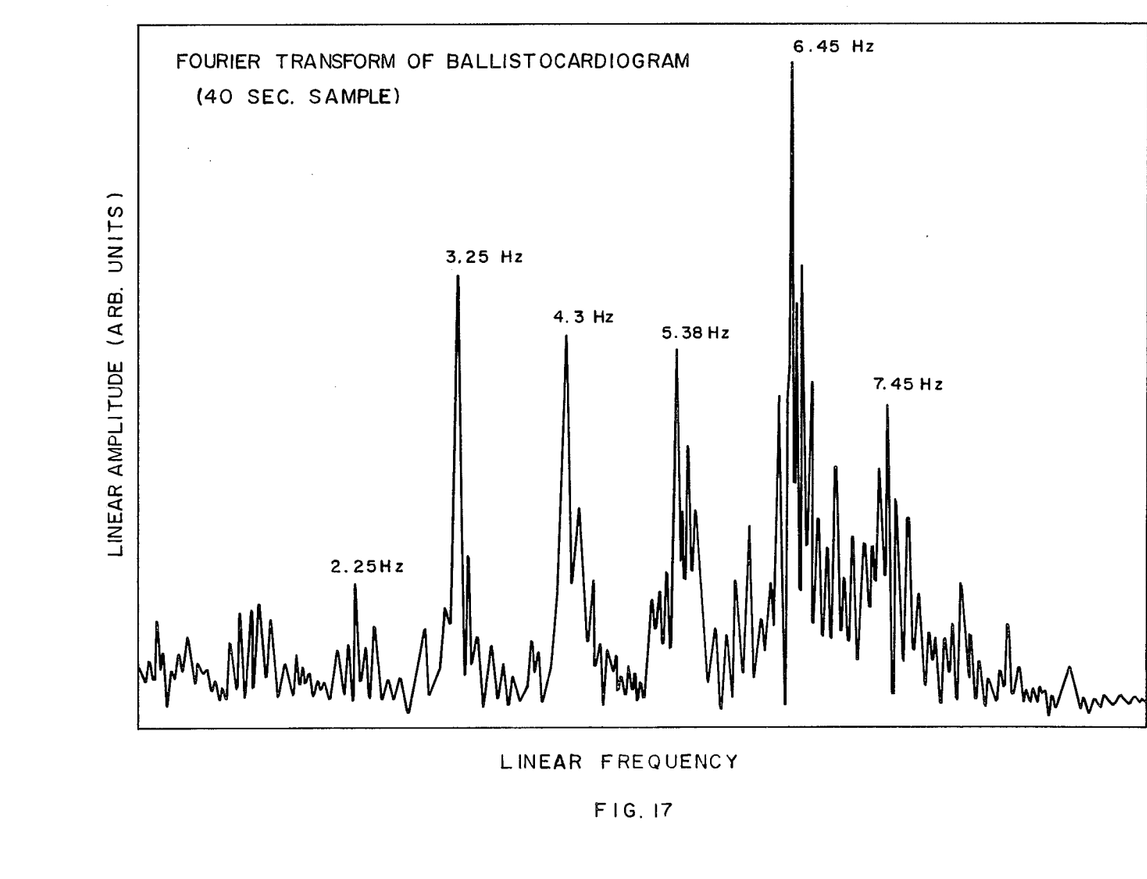
FIG. 17 is Fourier transform of a force ballistocardiagram.

Data such as that shown in FIG. 13 can be Fourier transformed with the result shown in FIG. 17. One observes here the largest Fourier amplitudes at harmonics of the pulse frequency 1/T, in this case at approximately 1.1 Hz. The envelope of the Fourier amplitudes peaks at the natural undamped frequency $\Omega_n$ of the system and in the circuit model is given by $$\omega_n^2 = \left(\frac{R_L + R_{th}}{R_{th}}\right)\frac{1}{LC}$$

and the width of the envelope is related to the damping constant $\zeta$ which in the circuit model is $$\zeta = \frac{1}{2}\sqrt{\frac{R_{th}R_LC - L)^2}{(R_{th} + R_L)R_{th}LC}}$$

By integrating the current i (t) over one pulse, i.e., $$\int_o^T i(t)dt,$$

(t)dt, one obtains the volume of blood pumped per pulse, i.e., the stroke volume, (S.V.) and multiplying this by the pulse frequency one obtains the cardiac output. The mass of blood pumped per pulse is proportional to $$\left(\frac{L}{R_{th} + R_L}\right) \int_o^T V_{th}(t)\, dt$$

The individual circuit parameters L, $R_L$, $R_{th}$, and C can be obtained by measuring $V_{th}$(t) and fitting the response of the circuit model as shown in FIG. 13 and its Fourier transform as shown in FIG. 17 to the circuit response. Thus the force plate system can give a non-invasive indication of the stroke volume and cardiac output. The method of extracting this information is totally apart from the empirical formula developed by I. Starr (1939, 1958), i.e., S.V.=60√(2 area I+area J)√T where area I and area J are the areas under respective parts of the ballistocardiogram in mm-sec.

The stroke-volume and cardiac output are well known to be important parameters describing the state of the cardiovascular system. The method and results advanced here offer two new pieces of information, the undamped natural frequency $\Omega_n$ and the damping $\zeta$ as giving further relevant information.

Figure 14:
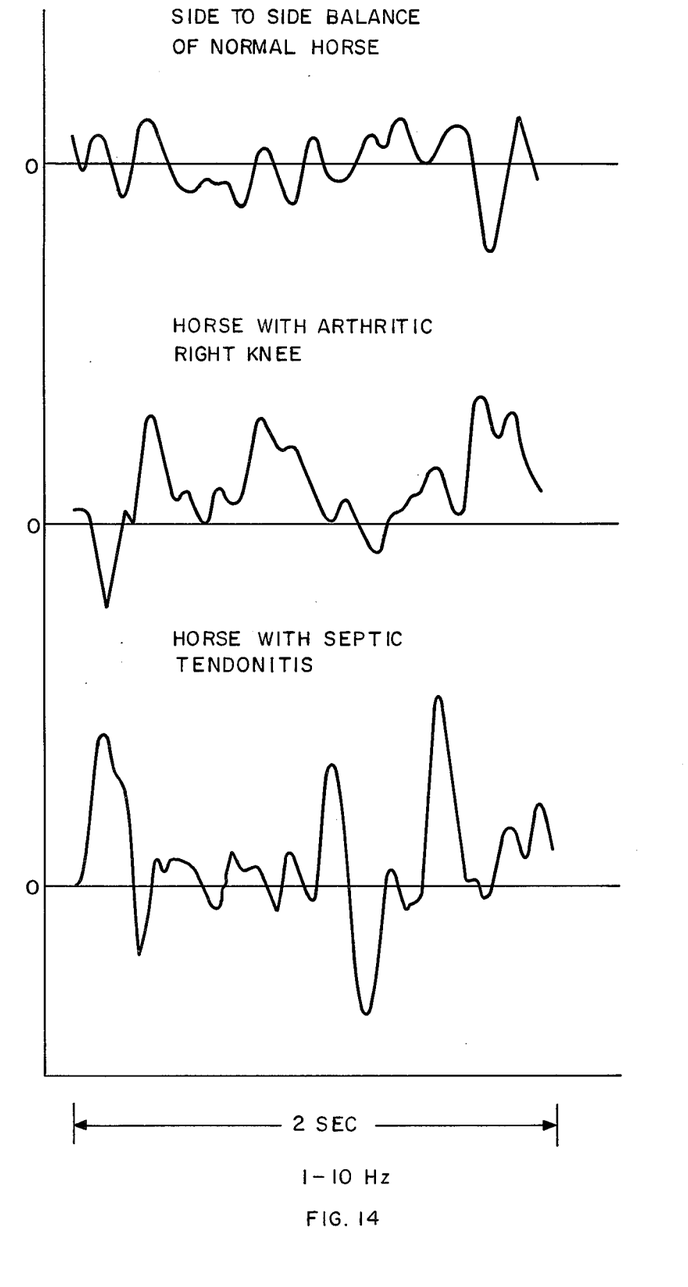
FIG. 14 shows three balance force vs. time traces of three separate horses.

In FIG. 14 there is shown balance force information taken on three separate horses using two force plates and displaying the difference $F_1-F_2$. The top trace in FIG. 14 shows the balance trace for a normal horse, the middle trace that for a horse with an arthritic right knee, and, finally, the bottom trace that of a horse with septic tendonites. The degree of distress progresses from top to bottom in FIG. 14. An important problem is that of quantifying the degree of lameness or posture control distress. This can be done by taking the root mean square balance force signal or by computing the amplitude histogram of the balance force. (See a journal article entitled, "Force Plate Studies of Equine Biomechanics," Pratt et al., Am. J. Vet. Res., Vol. 37, 11, November 1976, pp. 1251-1255 for a further discussion of studies done in connection with horses.)

Figure 18:
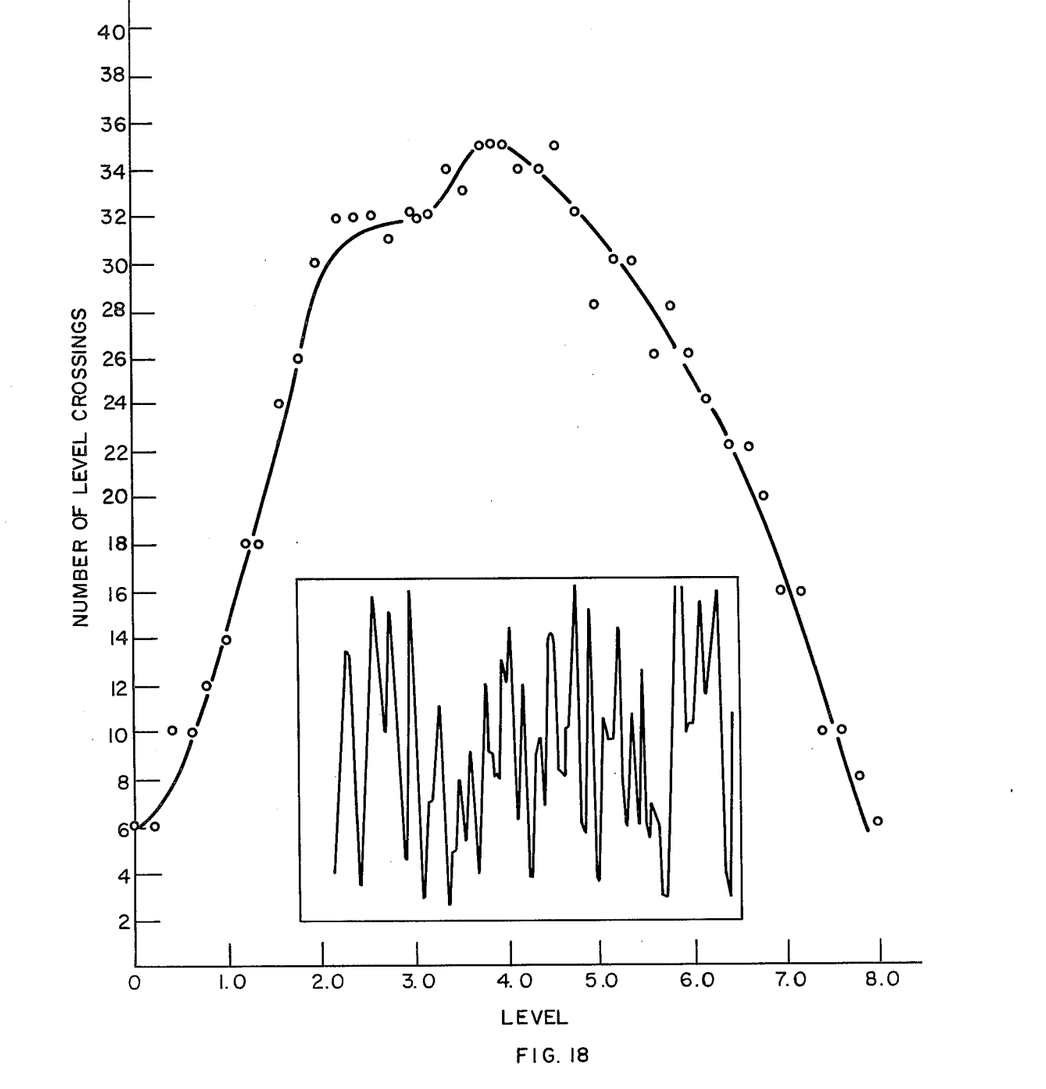
FIG. 18 is a force amplitude histogram taken of the right front leg of a horse standing on a wedge that artificially raises the heel of the foot.
Figure 19:
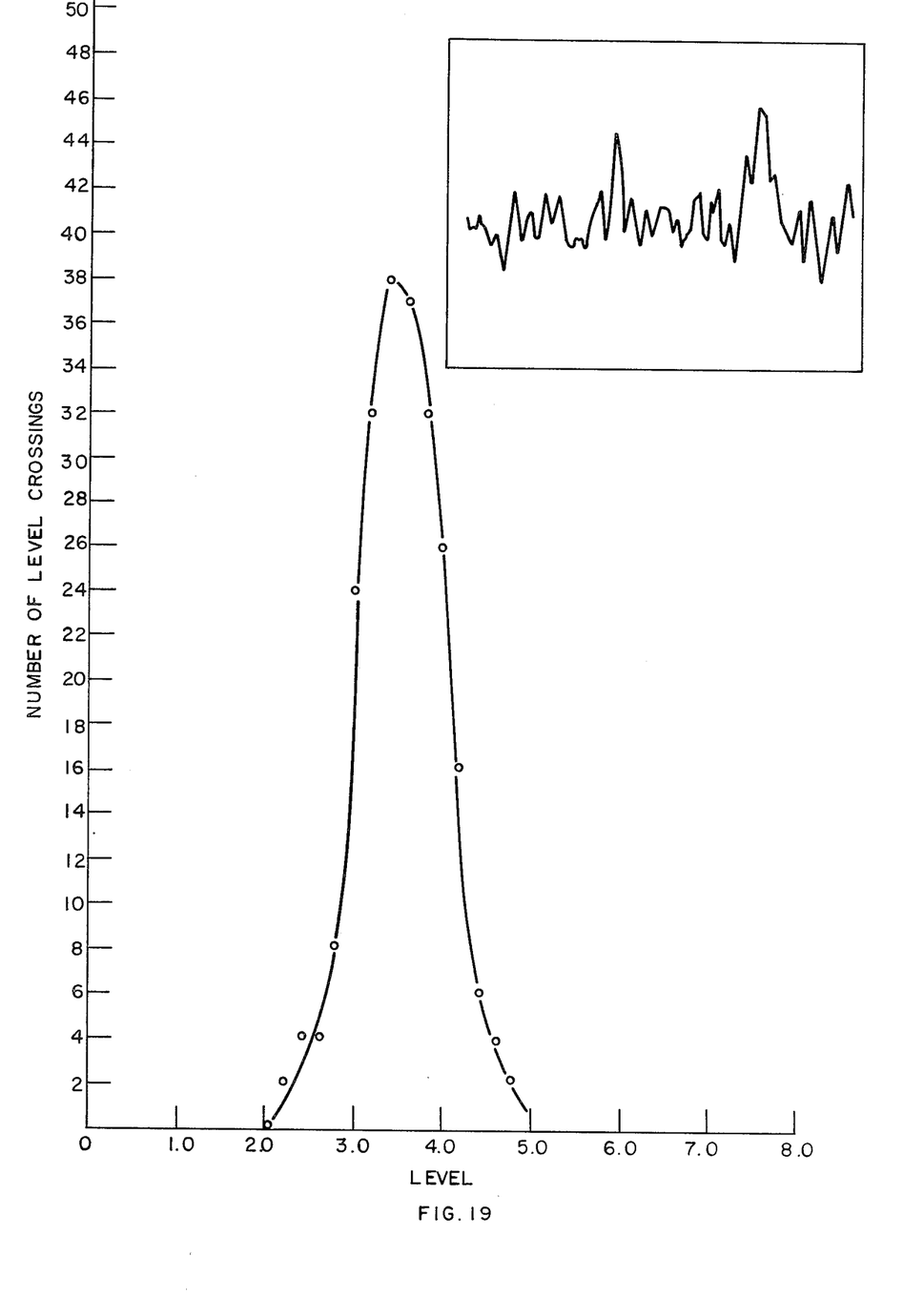
FIG. 19 is a force amplitude histogram taken of the right front leg of a horse standing on a wedge that artificially lowers the heel of the foot.

FIG. 18 shows the amplitude histogram taken on a race horse named Del Ali standing with his right front foot on a wedge that raises the heel with respect to the toe, the wedge being on a force plate. The left front foot of the horse is held off the ground during this interval. The actual balance forces vs. time are shown in the insert in FIG. 18. These data are to be compared with that in FIG. 19 where the wedge was turned by 180° so that the toe is raised with respect to the heel. It is apparent that the distress level is markedly reduced by raising the toe. The histogram or the root means square balance force gives a measure of the energy expended to maintain posture control.

Figure 26:
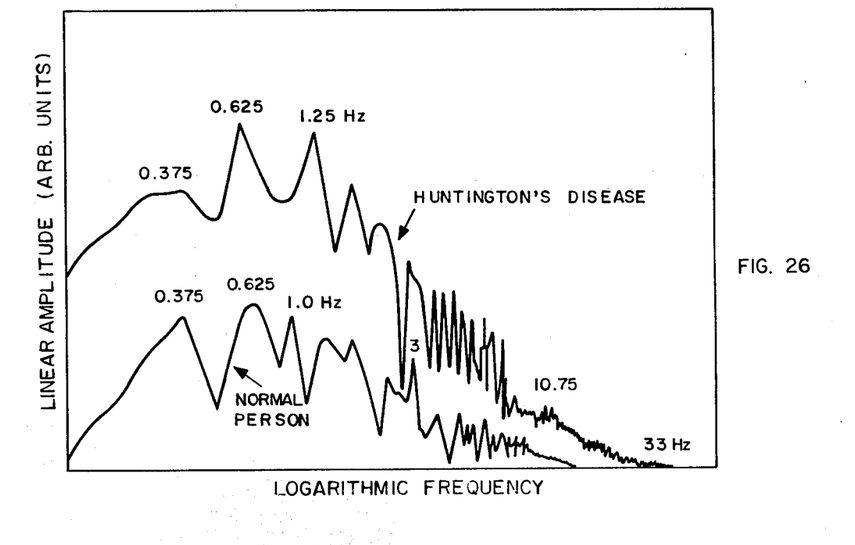
FIG. 26 shows the FFT of the balance forces of a normal person and one with Huntington's Disease.

Posture control forces can also be used to study various diseases as evidenced by the data shown in FIG. 15, FIG. 16 and FIG. 26. In FIG. 15, the balance force $F_1-F_2$ is shown for a normal person and one with Huntington's disease in a configuration using two force plates, one for each leg, and the signal filtered so that the 0.1-30 Hz band is accepted. It is apparent from FIG. 15 that the Huntington's disease patient transmits higher frequency signals where a tremor occurs. In FIG. 16 all signals below 10 Hz are attenuated by a filter. The normal person's balance force resembles background noise while the Huntington's patient shows signals characteristic of his condition. In FIG. 26 the FFT of the balance forces for a normal person and a Huntington's diseased person are shown. The frequency control of Huntington's disease balance forces is seen to extend significantly beyond that of a normal person. Related studies using a single force platform have been made by Wertzman et al. in a paper entitled, "Quantification of Chorea in Huntington's Disease by Power Spectral Analysis" that accompanies herewith.

Figures 25, 27:
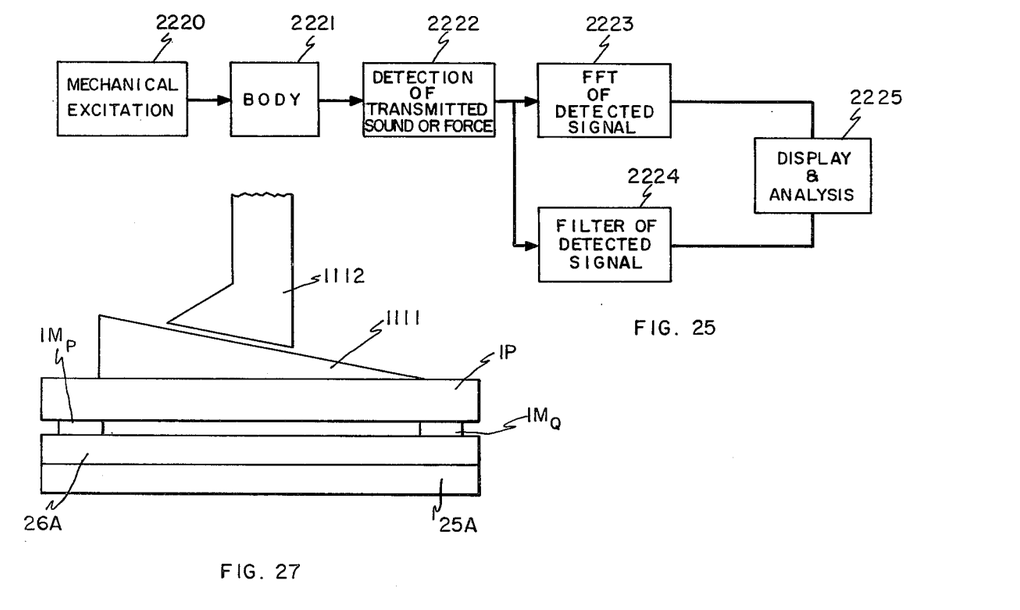
FIG. 25 shows in block diagram form the system used in obtaining the data shown in FIGS. 20 and 21.
FIG. 27 shows a horse's foot resting upon a wedge which is placed upon a force plate.

FIG. 27 shows a wedge 1111 upon which a horse's foot 1112 is placed. The wedge rests upon a force plate 1P having transducers $1M_p$, $1M_Q$..., a base plate 26A and an adapting pad 25A.

Figure 20:
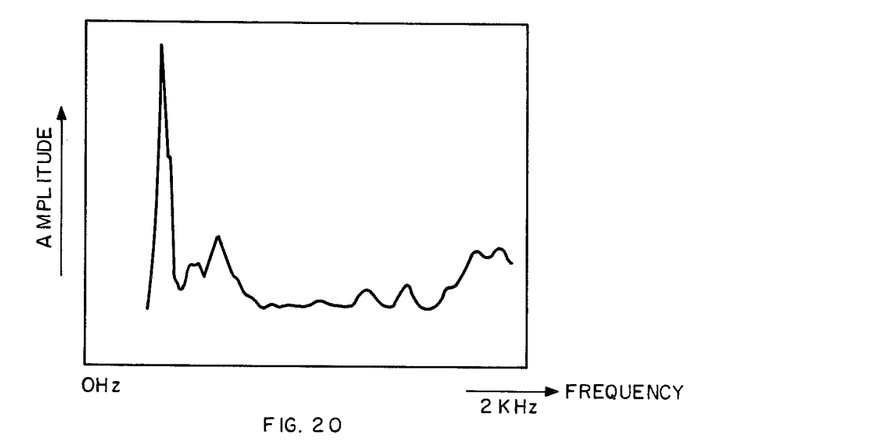
FIG. 20. is the amplitude of the Fourier transform plotted vs. frequency for the signal detected by a microphone coupled to the femur of a cadaver in which a total hip replacement has been made, in which the pin inserted into the femur is loose, in which the signal results from a mechanical impact on the hip, and in which the frequency scale is 0–2 kHz.
Figure 21:
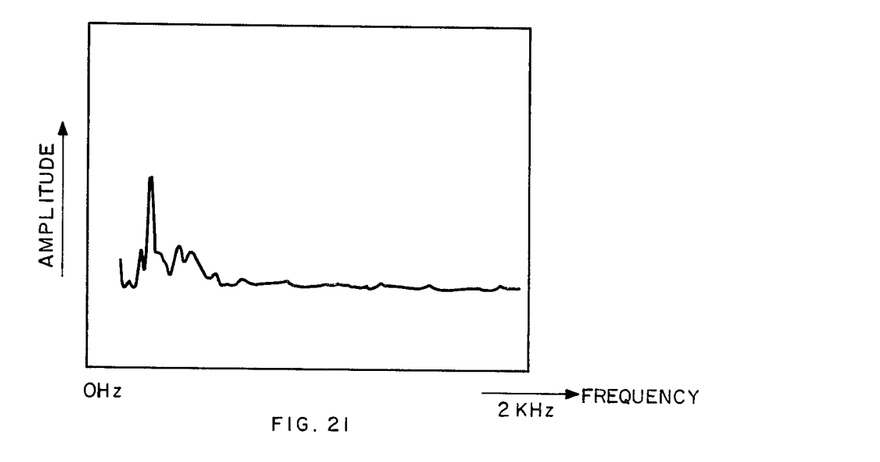
FIG. 21 is the same as FIG. 20 except that the inserted pin is tight.

Finally, in FIG. 20 and FIG. 21 the forces transmitted through the femur of a cadaver are shown when the hip joint of the cadaver has been totally replaced and the hip is excited by a mechanical impulse force and the transmitted force or sound detected using a cardiac microphone and the detected signal passed through a FFT device. In FIGS. 20 and 21 the ordinate is Fourier amplitude and the abscissa frequency. In the case of FIG. 20 the metallic pin used in the hip replacement is loose and the output of the FFT device shows a Fourier amplitude envelope above background in the vicinity of 200 Hz and again in the vicinity of 1600 Hz. This is characteristic of two loosely coupled oscillators, the bone resonating near 200 Hz and the pin near 1600 Hz. If the pin is tight, one has a single oscillator, that of the tightly coupled bone-pin. In this case there is no high frequency envelope since the bone and pin behave mechanically as a single system. FIG. 21 shows only a low frequency envelope. Hence, the FFT of the transmitted force signal provides a noninvasive means of evaluating the mechanical state of the implanted pin. The system is shown in block diagram form in FIG. 25. Here mechanical excitation means 2220 are applied to a body 2221 which may be a human or an animal. The transmitted forces or sounds are detected in block 2222 wherein one or more detectors may be employed. The output of 2222 is fed to an FFT device 2223 (e.g., PAR Model 4512, Real Time Spectrum Analyzer) or more simply to a filter 2224. simply to a filter 2224. The processed signal is displayed and analyzed at 2225.

The ceramic capacitor transducer discussed herein has been found to exhibit a marked pyroelectric effect and to act as a sensitive bolometer. The rapid variation in temperature of the dielectric constant of a ferroelectric near its transition temperature also contributes to a variation in capacitance that can be sensed. The capacitors used herein show a dynamic sensitivity to force of approximately $300 \times 10^{-12}$ coulombs/Newton and a sensitivity to temperature change of approximately $10^{-6}$ volts output for a dynamic temperature fluctuation of $50 \times 10^{-6}$° K.

Further modifications of the invention herein disclosed will occur to persons skilled in the art and all said modifications are deemed to be within the spirit and scope of the invention as defined by the appended claims.

What is claimed is:

1. A method of using diagnostic apparatus for measuring the relationship between distress level and physiological force due to pain developed by a live being, that comprises the steps of providing a force plate system comprising at least one force plate to receive said physiological forces supporting at least some portion of a live being on said at least one force plate operable to produce an analog output signal comprising a dc component and an ac component;

providing analyzer means connected to said analog output signal distinguishing between the dc component and the ac component thereby to produce an output signal derived from the ac component that quantifies said distress level; including the further step of preparing from the output signal a force amplitude hisogram over a predetermined time interval having a width indicating the level of distress due to pain.

2. A method as set forth in claim 1, including repeating said steps for individual limbs of a live being and comparing the respective histograms to detect lameness due to pain.

3. A method of using diagnostic apparatus for measuring the relationship between distress level and physiological force due to pain developed by a live being, that comprises the steps of providing a force plate system comprising at least one force plate to receive said physiological forces supporting at least some portion of a live being on said at least one force plate operable to produce an analog output signal comprising a dc component and an ac component;

providing analyzer means connected to receive said analog output signal distinguishing between the dc component and the ac component thereby to produce an output signal derived from the ac component that quantifies said distress level; including the further step of preparing a root means square average of the output signal as a measure of distress level indicating pain.

4. In a method as set forth in claim 3, including repeating said steps for individual limbs of a live being and comparing the respective root mean square averages to detect lameness due to pain.

* * * * *